(12) United States Patent
Matsuda et al.

(10) Patent No.: US 7,736,707 B2
(45) Date of Patent: Jun. 15, 2010

(54) BIREFRINGENT FILM, POLYCYCLIC COMPOUND, COATING LIQUID, AND IMAGE DISPLAY DEVICE

(75) Inventors: Shoichi Matsuda, Osaka (JP); Junzo Miyazaki, Osaka (JP)

(73) Assignee: Nitto Denko Corporation, Ibaraki-Shi, Osaka (JP)

( * ) Notice: Subject to any disclaimer, the term of this patent is extended or adjusted under 35 U.S.C. 154(b) by 122 days.

(21) Appl. No.: 12/049,582

(22) Filed: Mar. 17, 2008

(65) Prior Publication Data

US 2008/0224095 A1  Sep. 18, 2008

(30) Foreign Application Priority Data

Mar. 16, 2007  (JP) .............................. 2007-067839

(51) Int. Cl.
*C09K 19/52* (2006.01)
*C09K 19/32* (2006.01)
*C09K 19/34* (2006.01)
*G02B 5/30* (2006.01)
*G02F 1/13363* (2006.01)
*C07D 241/38* (2006.01)

(52) U.S. Cl. .............. 428/1.1; 252/299.01; 252/299.61; 252/299.62; 544/342

(58) Field of Classification Search .................. 428/1.1; 252/299.01, 299.61, 299.62; 544/342
See application file for complete search history.

(56) References Cited

U.S. PATENT DOCUMENTS

2005/0109986 A1* 5/2005 Dutova et al. .......... 252/299.01
2008/0206597 A1* 8/2008 Iwakuma .................... 428/690

FOREIGN PATENT DOCUMENTS

WO  WO 2007029806 A1 *  3/2007

* cited by examiner

*Primary Examiner*—Shean C Wu
(74) *Attorney, Agent, or Firm*—Westerman, Hattori, Daniels & Adrian, LLP (57) ABSTRACT

The present invention provides a birefringent film that hardly generates cracks even when the film is exposed under a high-temperature and high-humidity environment for a long period of time. The birefringent film of the present invention is a film containing, as a major component, a lyotropic liquid crystalline polycyclic compound containing an acenaphtho[1,2-b]quinoxaline derivative unit in a molecular structure and having a molecular weight of 500 or higher. The birefringent film of the present invention preferably has a refractive index ellipsoid showing a relationship of $nx \geq nz > ny$, and more preferably has an in-plane birefringence of 0.01 or higher at the wavelength of 590 nm.

12 Claims, 1 Drawing Sheet

Fig. 1

BIREFRINGENT FILM, POLYCYCLIC COMPOUND, COATING LIQUID, AND IMAGE DISPLAY DEVICE

BACKGROUND OF THE INVENTION

1. Field of the Invention

The present invention relates to a birefringent film that is suitable as an optical member of an image display device, as well as to a polycyclic compound, a coating liquid, and the like that are used as a material for forming the birefringent film.

2. Description of the Related Art

A liquid crystal displaying device is a device that displays characters and images by using an electrooptical property of a liquid crystal molecule. As an optical member that is used in an image display device such as a liquid crystal displaying device, there are known a polarizing element that can pick up a specific polarized light and a birefringent film that causes a predetermined retardation. Here, the polarizing element is also referred to as a polarizer, a polarizing film, or the like. The birefringent film is also referred to as a retardation film, an optical compensating layer, or the like.

For the birefringent film, a polymer film, a film containing a liquid crystalline compound, or the like is generally used.

Conventionally, a birefringent film using a lyotropic liquid crystalline compound is known. Such a lyotropic liquid crystalline compound exhibits a liquid crystalline phase in a solution state. Therefore, a thin coated film as compared with a polymer film (namely, a thin birefringent film) can be formed by preparing a coating liquid containing the above-described liquid crystalline compound into a liquid crystalline phase and applying this coating liquid onto a suitable base material, followed by drying (See Japanese Patent Application Laid-Open (JP-A) No. 2002-241434).

SUMMARY OF THE INVENTION

However, a coated film formed from a coating liquid containing the above-described lyotropic liquid crystalline compound raises a problem of generating cracks when the film is exposed under a high-temperature environment or under a high-temperature and high-humidity environment for a long period of time. In particular, a birefringent film is used, for example, as an optical member of a display to be mounted on a vehicle, a liquid crystal television set, or the like. Such a display to be mounted on a vehicle or the like is placed at a location that can be at a comparatively high temperature. Therefore, in a birefringent film, there is demanded an excellent durability that hardly generates cracks and the like even when the film is exposed under a high-temperature environment.

An object of the present invention is to provide a birefringent film that hardly generates cracks even when the film is exposed under a high-temperature environment or under a high-temperature and high-humidity environment for a long period of time.

Also, another object of the present invention is to provide a polycyclic compound and a coating liquid that can be used for forming the above-described birefringent film.

The present invention provides a birefringent film comprising a lyotropic liquid crystalline polycyclic compound containing an acenaphtho[1,2-b]quinoxaline derivative unit in a molecular structure and having a molecular weight of 500 or higher.

The birefringent film of the present invention substantially does not generate cracks even when the film is exposed under a high-temperature environment or under a high-temperature and high-humidity environment for a long period of time, and therefore is excellent in durability. Such a birefringent film is especially useful, for example, as an optical member for an image display device that is placed at a location that can be at a comparatively high temperature.

In a preferable embodiment of the birefringent film of the present invention, the polycyclic compound contains a compound represented by the following general formula (I).

[CHEMICAL FORMULA 1]

(1)

In the formula (I), $A_1$, $A_2$, $X_1$, and $X_2$ each independently represent —COOM, —SO$_3$M, —PO$_3$M, —OH, or —NH$_2$; $B_1$, $B_2$, $Y_1$, and $Y_2$ each independently represent a halogen atom, an alkyl group having 1 to 4 carbon atoms, an alkoxy group having 1 to 4 carbon atoms, —OCOCH$_3$, —NHCOCH$_3$, —NO$_2$, —CF$_3$, —CN, —OCN, —SCN, —COOM, or —CONH$_2$; M represents a counter ion; Z represents a covalent bond, —O(C$_2$H$_4$O)$_{1-4}$—, —O—, —CO—O—(CH$_2$)$_{1-4}$—O—CO—, —CO—NH—(CH$_2$)$_{1-4}$—NH—CO—, —NH—CO—(CH$_2$)$_{1-4}$—CO—NH—, or an alkyl chain having 1 to 4 carbon atoms; k1, k2, l1, and l2 are each independently an integer of 0 to 3; m1, m2, n1, and n2 are independently an integer of 0 to 6; k1, k2, l1, l2, m1, m2, n1, and n2 are not simultaneously 0; and at least one of k1, k2, n1, and n2 is 1 or larger.

Preferably, k1=k2, l1=l2, m1=m2, and n1=n2 in the general formula (I).

A birefringent film containing a polycyclic compound of the above formula (I) hardly generates cracks and moreover is excellent in transparency. Further, the birefringent film has a high in-plane birefringence ($\Delta n_{xy}$) and hence has a predetermined retardation value even with a comparatively small thickness.

In another preferable embodiment of the birefringent film of the present invention, a transmittance at the wavelength of 590 nm is 85% or larger.

In another preferable embodiment of the birefringent film of the present invention, a refractive index ellipsoid shows a relationship of nx≧nz>ny.

In another preferable embodiment of the birefringent film of the present invention, an in-plane birefringence at the wavelength of 590 nm ($\Delta n_{xy}$[590]) is 0.01 or higher.

In another preferable embodiment of the birefringent film of the present invention, a thickness is 10 μm or smaller.

Further, the present invention provides a lyotropic liquid crystalline polycyclic compound containing an acenaphtho[1,2-b]quinoxaline derivative unit in a molecular structure and having a molecular weight of 500 or higher.

As the above-described lyotropic liquid crystalline polycyclic compound, a polycyclic compound represented by the above general formula (I) is preferable.

The above-described birefringent film of the present invention can be obtained by forming the lyotropic liquid crystalline polycyclic compound of the present invention into a film.

Therefore, the polycyclic compound of the present invention is particularly useful as a material for forming a birefringent film that hardly generates cracks.

Further, since the above-described polycyclic compound is water-soluble, a coating liquid can be prepared by dissolving the compound into an aqueous solvent.

In a preferable embodiment of the polycyclic compound of the present invention, the polycyclic compound is obtained by dimerization reaction of a monomer containing an acenaphtho[1,2-b]quinoxaline derivative.

In another preferable embodiment of the polycyclic compound of the present invention, the polycyclic compound is obtained by reaction of an aromatic tetraamine compound with an acenaphthenequinone derivative.

Further, the present invention provides a coating liquid containing any one of the above-mentioned polycyclic compound and water, and showing a liquid crystalline phase.

The above-described birefringent film can be produced with ease by applying such a coating liquid onto a suitable base material, followed by drying. For this reason, the coating liquid of the present invention is particularly useful as a material for forming a birefringent film that hardly generates cracks.

In preferable embodiment of the coating liquid of the present invention, a concentration of the polycyclic compound is 5 mass % to 40 mass %.

Further, the present invention provides an image display device provided with any one of the above-mentioned birefringent film.

An image display device provided with the birefringent film of the present invention is particularly useful for the purpose of being placed at a location that can be at a high temperature, such as a display to be mounted on a vehicle.

DETAILED DESCRIPTION OF THE PREFERRED EMBODIMENTS

Birefringent Film and Lyotropic Liquid Crystalline Polycyclic Compound of the Present Invention The birefringent film of the present invention is a film containing a lyotropic liquid crystalline polycyclic compound containing an acenaphtho[1,2-b]quinoxaline derivative unit in a molecular structure and having a molecular weight of 500 or higher.

Here, the birefringent film refers to a film having a refractive index anisotropy within a plane thereof and/or in a thickness direction, thereby generating a retardation.

As the above-described polycyclic compound, a compound having a molecular weight of 500 or higher is used so that substantially no cracks may be generated in the birefringent film under a high-temperature environment or under a high-temperature and high-humidity environment. The reason why cracks are hardly generated in the birefringent film by using the polycyclic compound having a molecular weight of 500 or higher is not definite. However, the present inventors infer that this is because flexibility is imparted to the film by using the above-described polycyclic compound.

The polycyclic compound preferably has a molecular weight of 600 or higher, more preferably a molecular weight of 800 or higher.

Meanwhile, the upper limit of the molecular weight of the polycyclic compound is not particularly limited. Nevertheless, the above-described polycyclic compound preferably has a molecular weight of 1,500 or lower, more preferably a molecular weight of 1,400 or lower, because then the polycyclic compound is excellent in water solubility and can exhibit a stable liquid crystalline phase.

The above polycyclic compound contains an acenaphtho[1,2-b]quinoxaline derivative as a basic skeleton. The acenaphtho[1,2-b]quinoxaline derivative preferably has at least one of —$SO_3M$ group and —COOM group. Here, the above-described M represents a counter ion.

By using a polycyclic compound containing the above-described derivative, a birefringent film having a high in-plane birefringence ($\Delta n_{xy}$) can be obtained.

Examples of the polycyclic compound of the present invention include an acenaphtho[1,2-b]quinoxaline derivative represented by the following general formula (I).

[CHEMICAL FORMULA 2]

(I)

In the formula (I), $A_1$, $A_2$, $X_1$, and $X_2$ each independently represent —COOM, —$SO_3M$, —$PO_3M$, —OH, or —$NH_2$, $B_1$, $B_2$, $Y_1$, and $Y_2$ each independently represent a halogen atom, an alkyl group having 1 to 4 carbon atoms, an alkoxy group having 1 to 4 carbon atoms, —$OCOCH_3$, —NH-$COCH_3$, —$NO_2$, —$CF_3$, —CN, —OCN, —SCN, —COOM, or —$CONH_2$. M represents a counter ion. Z represents a covalent bond, —$O(C_2H_4O)_{1-4}$—, —O—, —CO—O—$(CH_2)_{1-4}$—O—CO—, —CO—NH—$(CH_2)_{1-4}$—NH—CO—, —NH—CO—$(CH_2)_{1-4}$—CO—NH—, or an alkyl chain having 1 to 4 carbon atoms. Suffixes k1, k2, l1, l2, m1, m2, n1, and n2 represent the number of substitutions of the corresponding $A_1$, $A_2$, $B_1$, $B_2$, $Y_1$, $Y_2$, $X_1$, and $X_2$, respectively. The above-mentioned k1, k2, l1, and l2 are each independently an integer of 0 to 3, the above-mentioned m1, m2, n1, and n2 are independently an integer of 0 to 6, the above-mentioned k1, k2, l1, l2, m1, m2, n1, and n2 are not simultaneously 0, and at least one of k1, k2, n1, and n2 is 1 or larger.

Preferably, in the formula (I), k1=k2, l1=l2, m1=m2, and n1=n2, and the acenaphtho[1,2-b]quinoxaline derivative represented by the formula (I) is more preferably a dimer.

$A_1$, $A_2$, $X_1$, and $X_2$ in the formula (I) are preferably each independently —COOM, —$SO_3M$, or —$PO_3M$, and are more preferably —$SO_3M$ or —COOM. Also, it is preferable that the number of substitutions k1, k2 of $A_1$, $A_2$ in the formula (I) is 0 to 2, and the number of substitutions n1, n2 of $X_1$, $X_2$ in the formula (I) is 1 to 4.

Further, $B_1$, $B_2$, $Y_1$, and $Y_2$ in the formula (I) are preferably each independently a halogen atom, an alkyl group having 1 to 4 carbon atoms, or an alkoxy group having 1 to 4 carbon atoms. The number of substitutions thereof l1, l2, m1, m2 is preferably 0 to 2, more preferably 0 to 1. A polycyclic compound in which at least one of l1, l2, m1, and m2 in the formula (I) is not 0 has at least one of the substituents $B_1$, $B_2$, $Y_1$, and $Y_2$. Even if the polycyclic compound has these substituents, the water solubility does not decrease, and also the lyotropic liquid crystallinity is exhibited, so that a birefringent film being excellent in durability can be formed.

One preferable mode of the polycyclic compound of the present invention is a case in which the number of substitutions l1, l2 of $B_1$, $B_2$ represented by the above formula (I) is 0 (no substitutions). Such a polycyclic compound is an acenaphtho[1,2-b]quinoxaline derivative represented by the following formula (II).

[CHEMICAL FORMULA 3]

(II)

In the formula (II), $A_1$, $A_2$, $X_1$, $X_2$, $Y_1$, $Y_2$, Z, k1, k2, m1, m2, n1, and n2 are similar to those of the above formula (I). Also, k1, k2, m1, m2, n1, and n2 in the formula (II) are not simultaneously 0, and at least one of k1, k2, n1, and n2 is 1 or larger. Preferably, k1=k2, m1=m2, and n1=n2 in the formula (II), and the acenaphtho[1,2-b]quinoxaline derivative represented by the formula (II) is more preferably a dimer.

$A_1$, $A_2$, $X_1$, and $X_2$ in the formula (II) are preferably each independently —COOM, —$SO_3M$, or —$PO_3M$, and are more preferably —$SO_3M$ or —COOM. Also, it is preferable that the number of substitutions k1, k2 of $A_1$, $A_2$ in the general formula (II) is 0 to 2, and the number of substitutions n1, n2 of $X_1$, $X_2$ is 1 to 4.

Further, $Y_1$ and $Y_2$ in the formula (II) are preferably each independently a halogen atom, an alkyl group having 1 to 4 carbon atoms, or an alkoxy group having 1 to 4 carbon atoms. The number of substitutions thereof m1, m2 is preferably 0 to 2, and more preferably 0 to 1.

Moreover, Z in the formula (II) is preferably a covalent bond, —$O(C_2H_4O)_{1-4}$— or —O—, and is more preferably a covalent bond or —O—.

One preferable mode of the polycyclic compound of the present invention is a case in which the number of substitutions m1, m2 of $Y_1$, $Y_2$ represented by the above formula (II) is 0 (no substitutions). Such a polycyclic compound is an acenaphtho[1,2-b]quinoxaline derivative represented by the following formula (III).

[CHEMICAL FORMULA 4]

(III)

In the formula (III), $A_1$, $A_2$, $X_1$, $X_2$, Z, k1, k2, n1, and n2 are similar to those of the above formula (I). Also, k1, k2, n1, and n2 in the formula (III) are not simultaneously 0, and at least one of k1, k2, n1, and n2 is 1 or larger. Preferably, k1=k2, and n1=n2 in the formula (III), and the acenaphtho[1,2-b]quinoxaline derivative represented by the formula (III) is more preferably a dimer.

$A_1$, $A_2$, $X_1$, and $X_2$ in the formula (III) are preferably each independently —COOM, —$SO_3M$, or —$PO_3M$, and are more preferably —$SO_3M$ or —COOM. Also, it is preferable that the number of substitutions k1, k2 of $A_1$, $A_2$ in the general formula (III) is 0 to 2, and the number of substitutions n1, n2 of $X_1$, $X_2$ is 1 to 3.

Moreover, Z in the formula (III) is preferably a covalent bond, —$O(C_2H_4O)_{1-4}$— or —O—, and is more preferably a covalent bond or —O—.

One preferable mode of the polycyclic compound of the present invention is a case in which the number of substitutions k1, k2 of $A_1$, $A_2$ represented by the above formula (III) is 0 (no substitutions). Such a polycyclic compound is an acenaphtho[1,2-b]quinoxaline derivative represented by the following formula (III).

[CHEMICAL FORMULA 5]

(IV)

In the formula (IV), $X_1$, $X_2$, Z, n1, and n2 are similar to those of the above formula (I). Also, n1, and n2 in the formula (IV) are not simultaneously 0, and at least one of n1, and n2 is 1 or larger. Preferably, n1=n2 in the formula (IV), and the acenaphtho[1,2-b]quinoxaline derivative represented by the formula (IV) is more preferably a dimer.

$X_1$, and $X_2$ in the formula (IV) are preferably each independently —COOM, —$SO_3M$, or —$PO_3M$, and are more preferably —$SO_3M$ or —COOM. Also, the number of substitutions n1, n2 of $X_1$, $X_2$ in the general formula (IV) are preferably 1 to 3, and are more preferably 1 to 2.

Moreover, Z in the formula (IV) is preferably a covalent bond, —$O(C_2H_4O)_{1-4}$— or —O—, and is more preferably a covalent bond or —O—.

A polycyclic compound in which Z in the formula (IV) is a covalent bond is represented by the following formula (V).

[CHEMICAL FORMULA 6]

(V)

M in the above-described —COOM, —$SO_3M$, or —$PO_3M$ represents an arbitrary counter ion. This M is preferably a hydrogen atom, an alkali metal atom, an alkali earth metal atom, a metal ion, or a substituted or non-substituted ammonium ion. Examples of the above-described metal ion include $Ni^{2+}$, $Fe^{3+}$, $Cu^{2+}$, $Ag^+$, $Zn^{2+}$, $Al^{3+}$, $Pd^{2+}$, $Cd^{2+}$, $Sn^{2+}$, $Co^{2+}$, $Mn^{2+}$, $Ce^{3+}$, and the like.

Here, in the case that the birefringent film is formed from an aqueous solution containing a polycyclic compound, for example, it is preferable to select a group that improves the solubility to water as the above-described M. A polycyclic compound in which such a group that improves the water solubility is introduced is easily dissolved into an aqueous solvent. After a birefringent film is formed by applying an aqueous solution of this compound onto a base material to form a film, the above-described group that improves the water solubility may be replaced with a group that is insoluble or slightly soluble to water so as to enhance the water resistance.

The polycyclic compounds represented by the above formulas (I) to (V) can be synthesized in accordance with the following Synthesis Example (a) or (b).

1) Synthesis Example (a)

Dimerization Reaction

The polycyclic compounds represented by the above formulas (I) to (V) can be obtained by allowing two acenaphtho[1,2-b]quinoxaline derivatives to react with a compound having two reactive functional groups. As the compound having two reactive functional groups, for example, a straight-chain diamine compound can be used. Examples of the diamine compound include 1,4-diaminobutane and the like. Examples of the acenaphtho[1,2-b]quinoxaline derivative include acenaphtho[1,2-b]quinoxaline having a substituent represented by $X_1$ or/and $Y_1$ in the above formula (I) and the like.

2) Synthesis Example (b)

Condensation Reaction

The polycyclic compounds represented by the above formulas (I) to (V) can be obtained by dehydration condensation of an aromatic tetraamine compound with an acenaphthenequinone derivative.

As the aromatic tetraamine compound, for example, benzidine having four $NH_2$ groups can be used. Examples of the benzidine include 3,3'-diaminobenzidine. The aromatic tetraamine compound may be non-substituted or may be substituted with a substituent represented by $A_1$ or/and $B_1$ in the above formula (I).

Examples of the acetonaphthenequinone derivative include non-substituted acetonaphthenequinone and acenaphthenequinone having a substituent represented by $X_1$ or/and $Y_1$ in the above formula (I).

Also, in the case that the polycyclic compound obtained in the above-described Synthesis Examples (a) and (b) does not have —$SO_3M$ (M represents the same counter ion as in the above) or in the case that, though the polycyclic compound has —$SO_3M$, if the number thereof increases, the above-described obtained polycyclic compound may be sulfonated in accordance with the needs.

The sulfonation process can be carried out by bringing the polycyclic compound into contact with sulfuric acid, fuming sulfuric acid, chlorosulfonic acid, or the like.

The above-described polycyclic compound is preferably a compound exhibiting a liquid crystal phase (namely, a lyotropic liquid crystal) in a solution state. Here, this liquid crystal phase is preferably a nematic liquid crystal phase in view of being excellent in the orientation property. This nematic liquid crystal phase includes those in which a supermolecule is formed and an organizer thereof is in a nematic state.

The birefringent film of the present invention can be fabricated, for example, by forming a solution containing the above polycyclic compound into a film. With use of the above polycyclic compound, a transparent birefringent film having a high in-plane birefringence and having no or little absorption in the visible light region can be formed by preparing the compound in a solution form and forming the solution into a film by using the solvent casting method. Here, a method of producing the birefringent film will be described below in detail.

The birefringent film of the present invention can be formed to be thin because it can be formed by applying a solution. Further, the birefringent film of the present invention has a refractive index ellipsoid satisfying a relationship of $nx \geq nz > ny$ ($nx > nz > ny$ or $nx = nz > ny$) and shows a high in-plane birefringence. For this reason, the birefringent film of the present invention has a desired retardation value with an outstandingly small thickness as compared with a conventional birefringent film.

Here, in the present specification, "$nx=nz$" includes a case in which $nx$ and $nz$ are substantially identical in addition to a case in which $nx$ and $nz$ are completely identical. The case in which $nx$ and $nz$ are substantially identical refers, for example, to a case in which $Rth[590]$ is from −10 nm to 10 nm, preferably from −5 nm to 5 nm.

Also, "$nx$" and "$ny$" denote the refractive indices in directions that are perpendicular to each other within the plane of the birefringent film (here, $nx \geq ny$), and "$nz$" denotes the refractive index in the thickness direction of the birefringent film.

The present inventors infer that the reason why the above-described birefringent film exhibits a high birefringence property is as follows. That is, since the above-described polycyclic compound is liable to form an associated body in a solution and the orderliness of the state in which this associated body is formed is high, the film formed from such a solution also exhibits a high orientation property. In particular, the above-described polycyclic compound having —$SO_3M$ group and/or —$COOM$ group exhibits a higher orientation property and hence is preferable. One of the functions of this —$SO_3M$ group and/or —$COOM$ group is to improve the solubility of the polycyclic compound into an aqueous solvent and to enable forming a film by the solvent casting method, and the other function is that a film having a refractive index ellipsoid satisfying the relationship of $nx \geq nz > ny$ can be formed by controlling the refractive index in a three-dimensional manner.

The single-body transmittance of the above-described birefringent film at the wavelength of 590 nm is preferably 85% or higher, more preferably 90% or higher. The thickness of the birefringent film is preferably 10 μm or smaller, more preferably 5 μm or smaller. The thickness of the birefringent film is preferably 0.05 μm or larger, more preferably 0.1 μm or larger.

The in-plane birefringence of the above-described birefringent film at the wavelength of 590 nm at 23° C. ($\Delta n_{xy}[590]=nx \cdot ny$) is preferably 0.01 or larger, more preferably 0.05 or larger, still more preferably 0.1 or larger. The upper limit of the same $\Delta n_{xy}[590]$ is preferably 0.5 or smaller. Here, this $\Delta n_{xy}[590]$ can be suitably adjusted within the above range by the molecular structure of the polycyclic compound. In particular, a birefringent film satisfying such a property can be formed by using a polycyclic compound having —$SO_3M$ group and/or —$COOM$ group.

The in-plane retardation value of the above-described birefringent film at the wavelength of 590 nm ($Re[590]$) can be set to be a suitable value in accordance with an object. The above $Re[590]$ is 10 nm or larger, preferably from 20 nm to 300 nm.

Here, the in-plane retardation value (Re[λ]) refers to the retardation value within the plane of a birefringent film at the wavelength of λ (nm) at 23° C. The Re[λ] can be determined by Re[λ]=(nx−ny)×d, where the thickness of the birefringent film is d (nm).

The Rth[590] of the above-described birefringent film can be set to be a suitable value within a range in which the refractive index ellipsoid satisfies the relationship of nx≧nz>ny. The difference between the in-plane retardation value (Re[590]) and the retardation value in the thickness direction (Rth[590]) of the birefringent film at the wavelength of 590 nm (Re[590]−Rth[590]) is preferably 10 nm to 200 nm, more preferably 20 nm to 200 nm. Here, the retardation value in the thickness direction (Rth[λ]) refers to the retardation value in the thickness direction of a birefringent film at the wavelength of λ (nm) at 23° C. The Rth[λ] can be determined by Rth[λ]=(nx−nz)×d, where the thickness of the birefringent film is d (nm).

The Nz coefficient of the above-described birefringent film is preferably 0 to 0.9, more preferably 0 to 0.8, still more preferably 0.1 to 0.7. When the Nz coefficient is within the above range, the birefringent film can be used for optical compensation of liquid crystal cells in various driving modes. Here, the Nz coefficient is a value calculated from Rth[590]/Re[590].

Also, the wavelength dispersion value (D) of the above-described birefringent film is preferably 1.05 or larger, more preferably 1.06 to 1.15. Here, the wavelength dispersion value (D) is a value calculated from the formula; D=Re[480]/Re[550]. Regarding the conventional birefringent film fabricated by stretching a polymer film, a film exhibiting such a sharp wavelength dependency has not been obtained. The birefringent film of the present invention exhibits a sharp wavelength dependency of retardation because the retardation value measured with light having a short wavelength is sufficiently larger than the retardation value measured with light having a long wavelength. Here, the numerical values shown above are numerical values measured in accordance with the measuring method of the following Example.

<Method of Producing a Birefringent Film and Coating Liquid of the Present Invention>

The birefringent film of the present invention can be obtained by applying a coating liquid containing the above-described polycyclic compound (solution containing a polycyclic compound) onto a suitable base material, followed by drying. Specifically, a method of producing the birefringent film includes the following steps A to G.

Step A: step of obtaining the above-described polycyclic compound.

Step B: step of dissolving the above-described polycyclic compound into an aqueous solvent to prepare a coating liquid.

Step C: step of preparing a base material in which at least an application surface has hydrophilicity.

Step D: step of applying the coating liquid onto the application surface of the above-described base material to form a coating film.

Step F: step of drying the above-described coating film.

Step G: step of bringing the surface of the above-described dried coating film into contact with a solution containing at least one kind of a compound salt selected from the group consisting of aluminum salt, barium salt, lead salt, chromium salt, strontium salt, and compound salts having two or more amino groups within a molecule.

(Step A)

The step A is a step of synthesizing the above-described polycyclic compound. Regarding the method thereof, one should make reference to the above-described Synthesis Example (a) and Synthesis Example (b) as well as to the following description of the Example.

(Step B)

The step B is a step of preparing a coating liquid.

The above-described polycyclic compound can be dissolved into an aqueous solvent. As the aqueous solvent, one can preferably use water.

The electric conductivity of the above-described water is preferably 20 µS/cm or smaller (lower limit value is 0 µS/cm), more preferably 0.001 µS/cm to 10 µS/cm, still more preferably 0.01 µS/cm to 5 µS/cm. By using a coating liquid in which the electric conductivity of water is within the above range, a birefringent film having a small thickness variation and being excellent in durability can be fabricated. Here, the above-described electric conductivity can be measured with use of a solution electroconductivity meter (Kyoto Electronic Manufacturing Co., Ltd., product name: CM-117).

Also, the aqueous solvent may contain other solvents in addition to water. Examples of the other solvents include alcohols, ethers, esters, ketones, cellosolves, and others. These other solvents may be used either alone or as a mixture of two or more kinds.

The coating liquid can be obtained by dissolving one kind of the above-described polycyclic compound or two or more kinds of the above-described polycyclic compounds having different structures into an aqueous solvent such as water. The concentration of the polycyclic compound in the coating liquid is not particularly limited. The concentration of the polycyclic compound in the coating liquid is preferably 5 mass % to 40 mass %, more preferably 5 mass % to 30 mass %, still more preferably 5 mass % to 20 mass %, because then the polycyclic compound exhibits a stable nematic liquid crystal phase in the solution. Here, the nematic liquid crystal phase can be confirmed and distinguished by the optical pattern of the liquid crystal phase that is observed by a polarization microscope.

Also, the above-described coating liquid is preferably adjusted to have a pH value of about 4 to 10, more preferably a pH value of about 6 to 8.

Further, into the coating liquid, an additive may be added. Examples of the additive include a plasticizer, a thermal stabilizer, an optical stabilizer, a lubricant, an antioxidant, an ultraviolet absorber, a flame retardant, a coloring agent, an antistatic agent, a compatibility improving agent, a crosslinking agent, and a thickening agent. The amount of addition of these additives is preferably larger than 0 and 10 parts by mass or smaller with respect to 100 parts by mass of the coating liquid.

Further, a surfactant may be added to the coating liquid. The surfactant is used for improving the wettability and the application property of the polycyclic compound onto the base material surface. As the surfactant, a nonionic surfactant is preferably used. The amount of addition of the surfactant is preferably larger than 0 and is 5 parts by mass or smaller with respect to 100 parts by mass of the coating liquid.

(Step C)

The step C is a step of preparing a base material in which at least the application surface has hydrophilicity.

The base material is used for uniformly developing the above-described coating liquid. The base material is not particularly limited as long as it can uniformly develop the coating liquid. Nevertheless, since a water-soluble coating liquid is applied, a base material in which the application surface (surface of the base material on which the coating liquid is applied) has hydrophilicity is preferable.

As the above-described base material, for example, a polymer film (film means to include those generally referred to as a sheet), a glass plate, or the like can be used. In a preferable embodiment, the base material is a single polymer film and, in another preferable embodiment, the base material is a laminate body containing a polymer film. This laminate body containing a polymer film is preferably such that the polymer film further contains an orientation film.

The above-described polymer film is not particularly limited, however, a film being excellent in transparency is preferable (for example, having a haze value of 5% or smaller).

Examples of the polymer film include a film formed from a polymer such as polyester type such as polyethylene terephthalate and polyethylene naphthalate; cellulose type such as diacetylcellulose and triacetylcellulose; polycarbonate type; acryl type such as polymethyl methacrylate; styrene type such as polystyrene and an acrylonitrile styrene copolymer; olefin type such as polyethylene, polypropylene, polyolefins having a cyclic or norbornene structure, and an ethylene propylene copolymer; vinyl chloride type; amide type such as nylon and aromatic polyamide; imide type such as polyimide; polyethersulfone type; polyetheretherketone type; polyphenylene sulfide type; vinyl alcohol type; vinylidene chloride type; vinyl butyral type; acrylate type; polyoxymethylene type; and epoxy type. Also, the above-described polymer film may be a film formed from a mixture containing two or more kinds of these polymers or the like. In addition, the above-described polymer film may be a laminate body of two or more polymer films.

As these polymer films, a stretched film having been subjected to a stretching process is preferably used.

The thickness of the above-described base material can be suitably designed in accordance with the strength and the like. However, in view of thickness reduction and weight reduction, the thickness is preferably 300 μm or smaller, more preferably 5 to 200 μm, still more preferably 10 to 100 μm.

In the case that the above-described base material contains an orientation film, this orientation film is preferably formed by performing an orientation process. Examples of the above-described orientation process include a mechanical orientation process such as a rubbing process, a chemical orientation process such as an optical orientation process, and the like.

The mechanical orientation process can be carried out by rubbing in one direction with a cloth or the like on one surface of the base material (or one surface of a suitable coating film formed on one surface of the base material). By this, an orientation film can be formed on one surface of the base material. Also, a stretched film having been subjected to a stretching process can be used. The coating film on which the rubbing process or the like is performed is not particularly limited, so that the above-described polymer exemplified as the polymer film for the above-described base material or the like can be used. The orientation film is preferably an imide type polymer in view of the orientation efficiency of the liquid crystalline compound.

The chemical orientation process can be carried out by forming an optical orientation film containing an orientation agent on one surface of the base material and radiating light onto the optical orientation film. By this, an orientation film can be formed on the base material. Examples of the orientation agent include polymers having a photoreactive functional group that generates a photochemical reaction such as a photoisomerization reaction, an optical ring-opening-closing reaction, a photodimerization reaction, a photodecomposition reaction, and an optical Fries rearrangement reaction, and the like. The above-described optical orientation film can be formed by dissolving an orientation agent into a suitable solvent to form a solution and applying this solution onto a base material.

In the case that the application surface of the above-described base material (the surface of the base material on which the coating liquid is applied) has low hydrophilicity, a hydrophilization process is carried out on this application surface in accordance with the needs.

The above-described hydrophilization process is, for example, a process of setting the contact angle of water to the application surface at 23° C. to be preferably 5° to 60°, more preferably a process of setting it to be 5° to 50°, still more preferably a process of setting it to be 5° to 45°. By setting the contact angle of water on the application surface of the base material to be within the above range, a birefringent film having a high in-plane birefringence and a small thickness variation can be fabricated.

The hydrophilization treatment can be any suitable method. For example, the hydrophilization treatment can be a dry treatment or a wet treatment. The dry treatment is, for example, a discharge treatment, e.g., a corona treatment, a plasma treatment, or a glow discharge treatment; a flame treatment; an ozone treatment; an UV ozone treatment; and an ionization active ray treatment, e.g., an ultraviolet treatment or an election beam treatment. The wet treatment is, for example, an ultrasonic treatment using a solvent such as water or acetone, an alkali treatment, or an anchor coat treatment. These treatments can be used alone or in combination of two or more thereof.

Preferably, the hydrophilization treatment is a corona treatment, a plasma treatment, an alkali treatment, or an anchor coat treatment.

The typical corona treatment is a treatment of modifying a surface of a base material by passing through the base material in a corona discharge. The typical plasma treatment is a treatment of modifying a surface of a base material by passing through the base material in a low temperature plasma. The typical ultrasonic treatment is a treatment of improving wettability of a base material by dipping a base material in water or an organic solvent, applying ultrasonic to the base material, and removing contaminants on a surface of the base material. The typical alkali treatment is a treatment of modifying a surface of a base material by dipping the base material in an alkali treatment solution prepared by dissolving a basic material in water or an organic solvent. The typical anchor coat treatment is to coat an anchor coat agent on a surface of a basic material.

Here, the order of performing the steps A to C is not particularly limited, so that for example the coating liquid of the step B may be prepared after the step C is performed in advance.

(Step D)

The step D is a step of applying the coating liquid on the application surface of the above-described base material so as to form a coating film containing a polycyclic compound.

The above-described coating liquid is applied on the application surface of the base material. By this, a coating film containing a polycyclic compound is formed on the base material. The thickness of the coating film is not particularly limited; however, the thickness is typically 1 μm to 100 μm.

As a method of applying the coating liquid, a coating method using a proper coater is properly used. The coater is, for example, a reverse roll coater, a positive rotation roll coater, a gravure coater, a rod coater, a slot die coater, a slot orifice coater, a curtain coater, or a fountain coater.

(Step F)

The step F is a step of drying the coating film formed in the step D.

The coating film formed in the step D and containing a polycyclic compound is dried by a suitable method. The drying can be carried out, for example, with use of an air-circulation thermostat oven in which hot air or cold air is circulated, a heater using a microwave, a far infrared ray, or the like, a roll heated for temperature regulation, a heated heat pipe roll, a heated metal belt, or the like.

The drying temperature is below or equal to the isotropic phase transition temperature of the solution, and the temperature is preferably raised gradually from a low temperature to a high temperature. The above-described drying temperature is preferably 10° C. to 80° C., more preferably 20° C. to 60° C. Within such a temperature range, a birefringent film being excellent in durability can be fabricated.

The period of time for drying can be suitably selected depending on the drying temperature and the kind of the solvent. In order to obtain a birefringent film being excellent in durability, the drying time is, for example, 1 minute to 30 minutes, preferably 1 minute to 10 minutes.

The amount of residual solvent in the obtained birefringent film is preferably 1 mass % or smaller, more preferably 0.5 mass % or smaller.

The coating film subjected to drying shows retardation, and the coating film subjected to drying will be the birefringent film of the present invention.

(Step G)

The step G is a step of imparting water resistance to the surface of the above-described coating film subjected to drying (the surface opposite to the surface bonded to the base material).

Specifically, the surface of the dried coating film formed in the above-described step F is brought into contact with a solution containing at least one kind of a compound salt selected from the group consisting of aluminum salt, barium salt, lead salt, chromium salt, strontium salt, and compound salts having two or more amino groups within a molecule.

Examples of the above-described compound salt include aluminum chloride, barium chloride, lead chloride, chromium chloride, strontium chloride, 4,4'-tetramethyldiamino-diphenylmethane hydrochloride, 2,2'-dipyridyl hydrochloride, 4,4'-dipyridyl hydrochloride, melamine hydrochloride, tetraminopyrimidine hydrochloride, and the like. By forming a layer of such a compound salt on the coating film surface, the surface of the coating film can be made insoluble or slightly soluble to water. Therefore, water resistance can be imparted to the coating film containing a polycyclic compound.

In the solution containing the above-described compound salt, the concentration of the compound salt is preferably 3 mass % to 40 mass %, more preferably 5 mass % to 30 mass %.

As a method of bringing the solution containing the above-described compound salt into contact with the surface of the above-described dried coating film, one can adopt, for example, a method of applying the solution containing the above-described compound salt onto the surface of the dried coating film, a method of immersing the coating film into the solution containing the above-described compound salt, or the like. In the case that these methods are adopted, the surface of the coating film is preferably dried in advance after being washed with water or an arbitrary solvent.

<Use of the Birefringent Film and the Like of the Present Invention>

The use of the birefringent film of the present invention is not particularly limited; however, it is representatively used as an optical member ($\lambda/4$ plate, $\lambda/2$ plate, viewing angle enlarging film, or the like) of a liquid crystal displaying device.

In one embodiment, the birefringent film of the present invention can be used in a form of a polarizing plate by laminating a polarizer onto this film.

The above-described polarizing plate includes at least the birefringent film of the present invention and a polarizer. This polarizing plate may include another optical laminate, another birefringent film, an arbitrary protective layer, and the like. For practical use, an arbitrary suitable bonding layer is disposed between the layers of the above-described polarizing plate, so as to bond the layers.

The polarizer is an optical member having a function of converting a natural light or a polarized light into a linearly polarized light. As the polarizer, an arbitrary suitable one can be adopted. As the polarizer, a stretched film having, as a major component, a polyvinyl alcohol type resin containing iodine or a dichroic dye is preferably used. The thickness of the above-described polarizer is typically 5 μm to 50 μm.

As the above-described bonding layer, an arbitrary suitable one can be selected as long as it bonds and integrates the surfaces of adjacent members with a practically sufficient bonding strength and a bonding time. Examples of the material for forming the above-described bonding layer include a bonding agent, a pressure-sensitive adhesive agent, and an anchor coat agent. The above-described bonding layer may be a multiple-layer structure in which an anchor coat agent layer is formed on a surface of a body to be bonded, and a bonding layer or a pressure-sensitive adhesive layer is formed thereon, or may be a thin layer (also referred to as a hair line) that is unrecognizable by a naked human eye. The bonding layer disposed on one side of the polarizer and the bonding layer disposed on the other side may be the same or may be different from each other.

Also, the birefringent film and the optical film containing the birefringent film of the present invention can be used as an optical member of various image display devices.

The image display device of the present invention includes an organic EL display, a plasma display, and others in addition to a liquid crystal displaying device. A preferable use of the image display device is a television set (particularly a large-scale television set having a screen size of 40 inches or more). In the case that the image display device is a liquid crystal displaying device, preferable uses thereof are OA apparatus such as a personal computer monitor, a notebook personal computer, and a copying machine; portable apparatus such as a portable telephone, a clock, a digital camera, a portable digital assistance (PDA), and a portable game machine; a home-use electric apparatus such as a video camera and an electronic range; apparatus to be mounted on a vehicle such as a back monitor, a monitor for a car navigation system, and a car audio device; an exhibition apparatus such as an information monitor for commercial shops; guarding apparatus such as a monitor for supervision; and assisting and medical apparatus such as a monitor for assisting senior persons and a monitor for medical use.

EXAMPLES

Hereafter, the present invention will be further described by showing Examples and Comparative Examples. However, it is to be noted that the present invention is not limited to these Examples. Here, the measuring methods used in Examples are as follows.

(1) Method of Measuring Thickness:

The thickness was measured by using a three-dimensional non-contact surface shape measuring system (manufactured by Ryoka Systems Inc., product name: "Micromap MM5200"), exfoliating a part of the coating film, and measuring the step difference between the coating film (birefringent film) and the base material (glass plate). The measured difference was regarded as the thickness.

(2) Method of Measuring nx, ny, nz, Re[590], Rth[590], and Nz Coefficient:

With use of the trade name "KOBRA21-ADH" manufactured by Ohji Scientific Instruments, nx, ny, nz, Re[590], Rth[590], and Nz coefficient were measured at 23° C. Here, as the average refractive index, a value obtained by measurement with use of Abbe refractometer (manufactured by Atago Co., Ltd., product name: "DR-M4") was used.

(3) Method of Measuring Single-Body Transmittance:

With use of a spectrophotometer (manufactured by Murakami Color Research Laboratory., product name: "DOT-3"), a single-body transmittance was measured under a condition of 23° C. Here, for the measured value of the single-body transmittance, the wavelength of 550 nm was used as a standard.

The single-body transmittance is a Y value of tristimulus value based on the two degree field of JIS Z 8701-1995.

Synthesis Example 1

Into a reaction vessel equipped with a stirrer, 50 g of dimethylformamide and 2.0 g of 3,3'-diaminobenzidine were added, and the mixture was stirred for 15 minutes. Into this mixture, 5.87 g of a mixture of acenaphthenequinone-2-sulfonic acid and acenaphthenequinone-3-sulfonic acid (equal amount in terms of the mass ratio) was added, and the resultant was stirred at room temperature for 24 hours for reaction (the following reaction formula (VI)). After the reaction was ended, 53.4 g of dimethylformamide was further added for dilution, and recrystallization was carried out with use of ethyl acetate. After being filtered, the obtained solid component was dried in vacuum for 24 hours. The yield was 86.1%. When the infrared spectroscopic spectrum of the purified product was measured, it was confirmed that the peaks (1739 cm$^{-1}$, 1713 cm$^{-1}$) of the acenaphthenequinone serving as a source material had disappeared, and the reaction had been completed.

The obtained purified product is [9,9']bi[acenaphtho[1,2-b]quinoxalinyl]disulfonate represented by the following formula (VI), and the molecular weight thereof is 666.7 as a free acid.

[CHEMICAL FORMULA 7]

(VI)

Example

Into 200 ml of ion exchange water, 5 g of the [9,9']bi[acenaphtho[1,2-b]quinoxalinyl]disulfonate obtained in the above Synthesis Example 1 was dissolved. The obtained aqueous solution was neutralized to pH=7 with 5 mass % aqueous solution of sodium hydroxide. Thereafter, the resultant was concentrated with use of a rotary evaporator until the concentration of the [9,9']bi[acenaphtho[1,2-b]quinoxalinyl] disulfonate would be 10.1 mass %, so as to prepare a coating liquid. Here, when observed with a polarization microscope, this coating liquid showed a nematic liquid crystal phase at 23° C.

In the meantime, both surfaces of a glass plate (manufactured by Matsunami Glass Ind., Ltd., having a thickness of 1.3 mm) were washed with use of a supersonic wave washer. The supersonic wave washing was carried out first in acetone for 3 minutes and then in ion exchange water for 5 minutes.

The above coating liquid was applied onto the surface of the orientation film of the above glass plate with use of a bar coater (manufactured by BUSCHMAN Co., Ltd., trade name: "mayer rot HS1.5"), followed by natural drying in a thermostat chamber at 23° C. to fabricate a birefringent film (coating film) having a thickness of 280 nm on the glass plate. Further, this birefringent film was immersed into 20 mass % aqueous solution of barium chloride and cleansed with ion exchange water to perform insolubilization process on the birefringent film.

The above-described birefringent film had a refractive index ellipsoid showing a relationship of nx>nz>ny, and various optical characteristics were as follows.

Single-body transmittance at the wavelength of 590 nm=91%.

In-plane birefringence at the wavelength of 590 nm ($\Delta n_{xy}$[590])=0.3.

Nz coefficient (Rth[590]/Re[590])=0.21.

In-plane retardation value at the wavelength of 590 nm (Re[590])=84 nm.

Retardation value in the thickness direction at the wavelength of 590 nm (Rth[590])=17 nm.

Two sheets of the samples of this birefringent film were prepared. One of these was put into a thermostat dryer at 90°

C., and the other one was put into a thermostat and humidistat dryer at 90° C./60% RH. The two were each stored for 220 hours, so as to perform a heat resistance test and a moisture resistance test.

Figure 1:
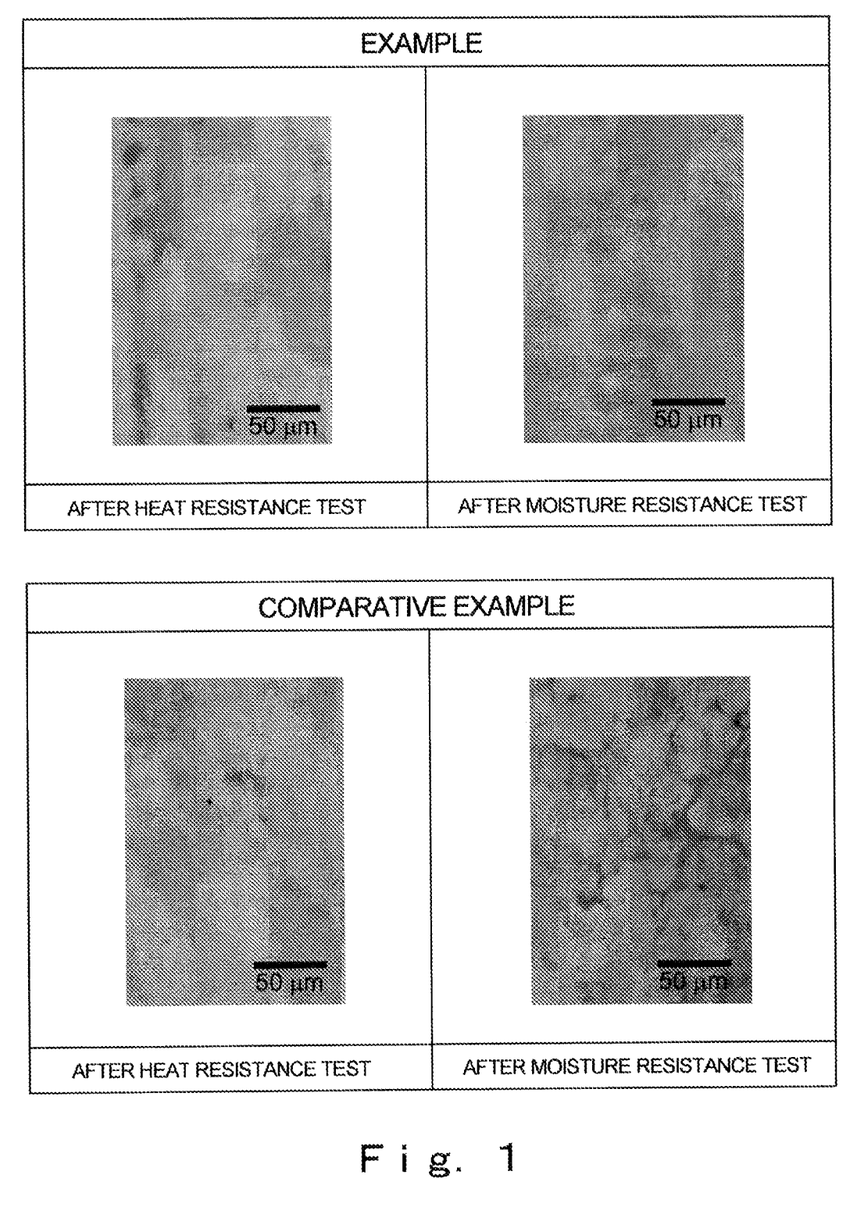
FIG. 1 is a surface photograph view of birefringent films of Example and Comparative Example after a test.

When the surface of the birefringent film after the test was observed with a polarization microscope, no cracks were observed. FIG. 1 shows an observed photograph view of the birefringent film according to the Example.

Synthesis Example 2

As represented by the following reaction formula (VII), after 30% fuming sulfuric acid (2.1 L) was added to 300 g of acenaphtho[1,2-b]quinoxaline and the mixture was stirred at room temperature for 24 hours, the resultant was heated to 130° C. and stirred for 32 hours for reaction. While keeping the obtained solution at 40° C. to 50° C., 4.5 L of ion exchange water was added for dilution, and the resultant was further stirred for 3 hours. The precipitate was filtered and recrystallized with sulfuric acid. After being washed with 1 L of acetone for three times, the resultant was filtered and subjected to vacuum drying at 60° C. for 12 hours to obtain acenaphtho[1,2-b]quinoxaline-2,5-disulfonic acid.

[CHEMICAL FORMULA 8]

(VII)

Synthesis Example 3

As represented by the following reaction formula (VIII), 30% fuming sulfuric acid (2.1 L) was added to 300 g of acenaphtho[1,2-b]quinoxaline and the mixture was stirred at room temperature for 48 hours for reaction. While keeping the obtained solution at 40° C. to 50° C., 4.5 L of ion exchange water was added for dilution, and the resultant was further stirred for 3 hours. The precipitate was filtered and, after being washed with 1 L of acetone for three times, the resultant was filtered and subjected to vacuum drying at 60° C. for 12 hours to obtain acenaphtho[1,2-b]quinoxaline-2-sulfonic acid.

[CHEMICAL FORMULA 9]

(VIII)

Comparative Example

After 52 g of the acenaphtho[1,2-b]quinoxaline-2,5-disulfonic acid obtained in Synthesis Example 2 and 28 g of the acenaphtho[1,2-b]quinoxaline-2-sulfonic acid obtained in Synthesis Example 3 were mixed, this mixture was dissolved into 780 mL of ion exchange water.

After the obtained aqueous solution was neutralized to pH=7.1 with 5% aqueous solution of sodium hydroxide, the resultant was concentrated to 25 mass % with use of a rotary evaporator to prepare a coating liquid.

This coating liquid was applied in the same manner as in the above-described Example, followed by drying to fabricate a birefringent film. The film was subjected to heat resistance test and moisture resistance test in the same manner.

When the birefringent film after the test was observed with a polarization microscope, fine cracks were observed in the whole area. FIG. 1 shows an observed photograph view of the birefringent film according to Comparative Example.

What is claimed is:
1. A birefringent film comprising a lyotropic liquid crystalline polycyclic compound represented by the following general formula (II):

(II)

wherein, $A_1$, $A_2$, $X_1$, and $X_2$ each independently represent —COOM, —SO$_3$M, —PO$_3$M, —OH, or —NH$_2$; $Y_1$, and $Y_2$ each independently represent a halogen atom, an alkyl group having 1 to 4 carbon atoms, an alkoxy group having 1 to 4 carbon atoms, —OCOCH$_3$, —NHCOCH$_3$, —NO$_2$, —CF$_3$, —CN, —OCN, —SCN, —COOM, or —CONH$_2$; M represents a counter ion; Z represents a covalent bond, —O(C$_2$H$_4$O)$_{1-4}$—, —O—, —CO—O—(CH$_2$)$_{1-4}$—O—CO—, —CO—NH—(CH$_2$)$_{1-4}$—NH—CO—, —NH—CO—(CH$_2$)$_{1-4}$—CO—NH—, or an alkyl chain having 1 to 4 carbon atoms; k1 and k2 are each independently an integer of 0 to 3; m1 and m2 are independently 0 or 1; n1 and n2 are independently an integer of 1 to 4.

2. The birefringent film according to claim 1, wherein k1=k2, m1=m2, and n1=n2 in said general formula (II).

3. The birefringent film according to claim 1, wherein a transmittance at the wavelength of 590 nm is 85% or larger.

4. The birefringent film according to claim 1, wherein a refractive index ellipsoid shows a relationship of nx≧nz>ny.

5. The birefringent film according to claim 1, wherein an in-plane birefringence at the wavelength of 590 nm ($\Delta n_{xy}$ [590]) is 0.01 or higher.

6. The birefringent film according to claim 1, wherein a thickness is 10 μm or smaller.

7. A lyotropic liquid crystalline polycyclic compound containing a compound represented by the following general formula (II):

(II)

wherein, $A_1$, $A_2$, $X_1$, and $X_2$ each independently represent —COOM, —SO$_3$M, —PO$_3$M, —OH, or —NH$_2$; $Y_1$, and $Y_2$ each independently represent a halogen atom, an alkyl group having 1 to 4 carbon atoms, an alkoxy group having 1 to 4 carbon atoms, —OCOCH$_3$, —NHCOCH$_3$, —NO$_2$, —CF$_3$, —CN, —OCN, —SCN, —COOM, or —CONH$_2$; M represents a counter ion; Z represents a covalent bond, —O(C$_2$H$_2$O)$_{1-4}$—, —O—, —CO—O—(CH$_2$)$_{1-4}$—O—CO—, —CO—NH—(CH$_2$)$_{1-4}$—NH—CO—, —NH—CO—(CH$_2$)$_{1-4}$—CO—NH—, or an alkyl chain having 1 to 4 carbon atoms; k1 and k2 are each independently an integer of 0 to 3; m1 and m2 are independently 0 or 1; n1, and n2 are independently an integer of 1 to 4.

8. The polycyclic compound according to claim 7, which is obtained by dimerization reaction of a monomer containing an acenaphtho[1,2-b]quinoxaline derivative.

9. The polycyclic compound according to claim 7, which is obtained by reaction of an aromatic tetraamine compound with an acenaphthenequinone derivative.

10. A coating liquid containing the polycyclic compound according to claim 7 and water, and showing a liquid crystalline phase.

11. The coating liquid according to claim 10, wherein a concentration of said polycyclic compound is 5 mass % to 40 mass %.

12. An image display device comprising the birefringent film according to claim 1.

* * * * *